US005776855A

United States Patent [19]
Schapira et al.

[11] Patent Number: 5,776,855
[45] Date of Patent: Jul. 7, 1998

[54] PHYTOSANITARY FLAKE COMPOSITIONS

[75] Inventors: Joseph Schapira, Paris; Jacques Vincent, Mareil Marly; Ange-Claude Guerin, Le Plessis Bouchard; Jean-Paul Fournials, Cergy Pontoise, all of France

[73] Assignee: CFPI AGRO, Gennevilliers, France

[21] Appl. No.: 679,757

[22] Filed: Jul. 10, 1996

[30] Foreign Application Priority Data

Jul. 13, 1995 [FR] France ................. 95 08569

[51] Int. Cl.$^6$ ............... A01N 25/34; A01N 37/34; A01N 33/18
[52] U.S. Cl. ............... 504/116; 504/310; 504/347; 34/110
[58] Field of Search ............... 504/116, 310, 504/347; 34/110

[56] References Cited

U.S. PATENT DOCUMENTS

| | | | |
|---|---|---|---|
| 3,820,970 | 6/1974 | Watkins | 71/1 |
| 4,235,993 | 11/1980 | Ramsey et al. | 252/548 |
| 4,832,730 | 5/1989 | Colgrove et al. | 71/92 |
| 5,593,948 | 1/1997 | Lisa et al. | 504/324 |

FOREIGN PATENT DOCUMENTS 2 218 634   5/1989   United Kingdom .

OTHER PUBLICATIONS

"Kirk–Othmer Encyclopedia of Chemical Technology", Wiley & Sons, 1989, XP002001028, 3rd Edition, vol. 21, pp. 95–96.

Central Patents Index, Basic Abstracts Journal, Week 8351 Derwent Publications Ltd., London, GB; AN 83-848659, XP002001029 & SU-A-239 713 (Yukhtin), Aug. 11, 1969.

Central Patents Index, Basic Abstracts Journal, Week 7320 Derwent Publications Ltd., London, GB; AN 83-28772U, XP002001030 & JP-A-73 015 614 (Tokyo Organic Chemicals Ind.), 1973.

*Primary Examiner*—S. Mark Clardy
*Attorney, Agent, or Firm*—Evenson, McKeown, Edwards & Lenahan, PLLC

[57] ABSTRACT

The invention relates to a new solid storage and marketing presentation for phytosanitary compositions based on any active substance which is little soluble in water or insoluble in water and solid at ambient temperature; these active substances are especially selected from herbicides presenting the said features; these herbicides comprise bramoxynil, ioxynil and their esters as well as, dinitroanilines, especially butralin, pendimethalin, flumetralin and oryzalin.

It is in the form of flakes based on a film-forming material which is water-soluble and brittle after drying, and throughout which are dispersed especially the particles of active material.

This solid storage and marketing presentation may be prepared by maly of an installation comprising a rotating drying drum (1) on which a thin layer of a dispersion (D) of particles of active substance in an aqueous solution of a film-forming material which is brittle at the dry state is applied.

The parties of the surface of the drum on which is applied the dispersion (D) travel through the heated part or zone of the chamber (2) at a speed such that the dispersion is dried, shrinks and becomes detached from the surface of the drum (1) in forming flakes (P).

9 Claims, 2 Drawing Sheets ns. 5,776,855

PHYTOSANITARY FLAKE COMPOSITIONS

The invention relates to a new solid storage and marketing presentation for phytosanitary cospositions.

It also relates to a process and an installation for its preparation.

It finally relates to its use for phytosanitary compositions based on any active substance which is little soluble in water or insoluble in water and solid at ambient temperature; these active substances are especially selected from herbicides presenting the said features and more especially from the group comprising bromoxynil, ioxynil and their esters, especially the octanoate, as well as dinitroanilines, especially butraline, pendimethalline, flumetraline and oryzalin, these compounds being possibly in combination with other herbicides.

Substances which are considered as solid at ambient temperature have a melting point higher than about 20° C. and more generally when they are in the solid state under temperature conditions in labs or in industrial environment.

Already known solid storage and marketing presentations for phytosanitary compositions are consisting of wettable or soluble powders, or granules which are diluted in water in the form of slurries in view of their application on the plants to be treated; these presentations have numerous drawbacks.

For instance, the wettable powders, in the case of active substances such as brotoxynil, besides their usual drawbacks among which way be their low density, their dusty character and their low fluence, present the irritating character of the active material when being prepared and during any later handling.

The drawbacks inherent to granules appear during their preparation.

In that connection, the usual methods of granulation, i.e. agglomeration by compacting, extrusion and granulation on rotating pan, comprise a first step which consists in a refining phase in the dry state of the product and a phase of agglomeration; due to that refining in the dry state, the drawbacks recited with respect to the wettable powders occur again, in particular their irritating action; consequently, their preparation raises problems in the field of hygiene and industrial security.

And even if, instead of the dry refining, recourse is made to a humid crushing in aqueous phase, the drawbacks inherent to powders appear again due to the fact that, in that case, a drying step by spraying is necessary in a spraying tower or in fluidized bed, due to which great amounts of -air or of neutral gas must be used and recycling operations become necessary as well as a granulometric selection and above all a recovery step for most small particles.

Consequently, an object of the invention is above all to overcome the drawbacks of the prior art and to provide the user with, on the one hand, a new solid storage and marketing presentation for phytosanitary compositions which is not dusty and, on the other hand, a process and an installation for the preparation of this new presentation which does not necessitate handling of powders of active substance.

And the Applicants have found, after extensive researches, that this object can be achieved as soon as the storage and marketing presentation for phytosanitary compositions is in the form of thin flakes which are dilutable in water and which are consisting of a film-forming material which is water-soluble and brittle after drying and throughout the mass of which are dispersed especially the particles of active material.

By way of consequence, the solid storage and marketing presentation for phytosanitary compositions according to the invention, based on any active substance which is little soluble in water or insoluble in water, solid at ambient temperature and especially selected from herbicides presenting these features, is characterized by the fact that it is in the form of fine flakes whose thickness is from about 50 to about 400 µm, preferably from 100 to 200 µm, whose largest measure or dimension is from about 2 to 20 mm, preferably from 5 to 10 mm and which are based on a film-forming material which is water-soluble and brittle after drying, and throughout which are dispersed especially the particles of active material whose largest dimension or measure is from 1 to 10 µm, preferably from 2 to 5 µm.

The process according to the invention for the preparation of the abovesaid solid storage and marketing presentation for phytosanitary compositions is characterized by the fact that a dispersion of particles of the active substance in an aqueous solution of a film-forming material which is water-soluble and brittle in the dry state and which also comprises the other components of the phytosanitary composition, is spread over a surface which is anti-adherent with respect to the said dispersion once dried in such a way that it forms a layer whose thickness is from 50 to 500 µm, preferably from 100 to 300 µm, the said layer being then subjected to a drying at a temperature from 35° to 150° C., the said layer, once dry, separating itself from the support forming thus the fine flakes according-to the invention.

The installation according to the invention for the preparation of the abovesaid solid storage and marketing presentation for phytosanitary compositions is characterized by the fact that it comprises, inside of an enclosed space or chamber, a rotating drying drum comprising a surface which is anti-adherent with respect to the product once dry, intented to be spread thereon, means adapted to apply continuously, inside a first zone which is not heated, of the enclosed space, at the surface of the drum, a thin layer of a dispersion of particles of active substance in an aqueous solution of a film-forming material, which is water-soluble and brittle at the dry state, and which also comprises the other components of the phytosanitary composition, heating means for the surface of the drum located inside a second zone of the enclosed space or chamber and inside a third zone means for recuperation of the thin flakes formed after drying of the layer of aqueous dispersion spread on the surface of the drum and means which are adapted to rotate the drum in such a way that the parties of the surface of the drum on which is applied the abovesaid dispersion travel through the heated part or zone of the chamber at a speed such that the dispersion is dried, shrinks and becomes detached from the surface of the drum, thus forming flakes.

The invention will even be better understood by way of the following description and the examples which are non-limiting and wherein are disclosed advantageous embodiments of the invention as well as by way of the drawings wherein.

Figure 1:
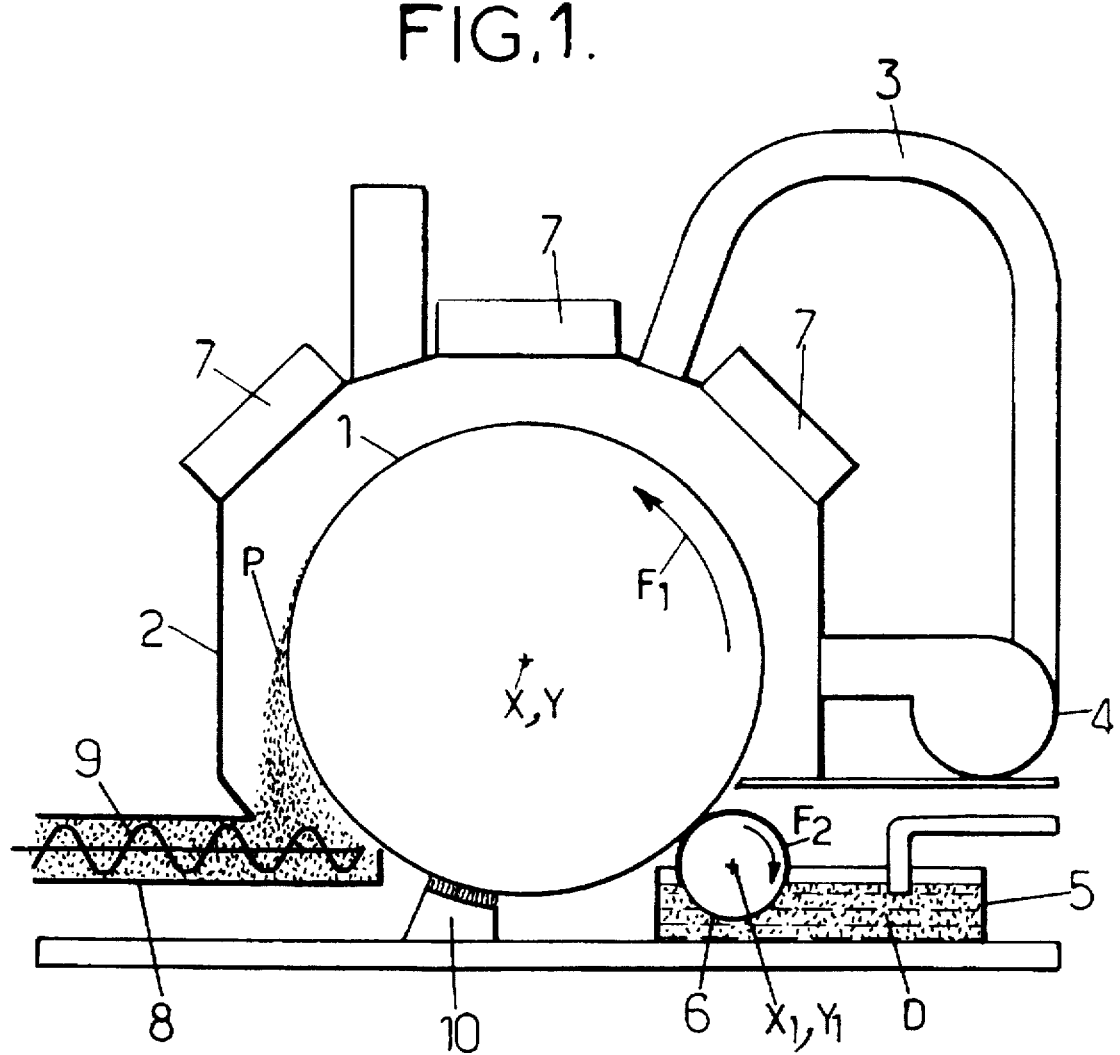
FIG. 1 shows a schematic view of an installation according to the invention.

In order to prepare a solid storage and marketing presentation for a phytosanitary composition wherein the active substance is selected among those which are little soluble or insoluble in water and which are solid at ambient temperature, these substances being especially selected among herbicides which present these features and sore especially from the group comprising bromoxynil and/or ioxynil and their esters, preferably octanoates, as well as dinitroanilines, preferably butraline, pendimethaline, flumetraline and oryzalin, these substances being possibly used in association with other herbicides, one way proceed as follows or in an equivalent manner.

It is to be underlined that it is possible to use, in a phytosanitary composition based on one or several of the abovesaid active substances, one or several other active substances which do not present the abovesaid features provided that the amount of these other substances introduced in the composition is lower than the amount which would provide the final product according to the invention with a sticky or waxy consistence.

Hereafter and by way of example, bromoxynil and butraline, possibly in association with other herbicides, have been used.

The bromoxynil as used was coarse, crystallized, technical grade bromoxynil, not completely dried, whose particle size was higher than 200 μm and lower than 1 m.

The butraline as used was technical butraline in the form of roughly crushed material whose particles size was below about 500 microns.

In order to prepare a formulation on the basis of one or the other of these two products, process ray be as follows.

The preparation is carried out in liquid phase by introduction into an agueous dispersion of the active substance, the constituents necessary for the crushing, the wetting agents and the dispersing agents which are possibly antifoaming and any other solid adjuvant necessitating a refining.

Avantageously, recourse is made to alkylaryl sulphates and/or sulphonates, to lignosulphonates, to polynaphthylmethanesulphonates and to polycarboxylates; polyethoxylated alkylphenols having a high molecular weight are also usable provided they are selected among those which will not trouble the drying and which will not provide the dry product with a sticky or waxy consistence.

The mixture is crushed, for example on a classical ball-mill, especially of glass or zirconium oxide, until obtention of a particle size adapted to provide the final diluted aqueous slurry which will be prepared by the user, with features satisfying from the point of view of stability of the suspension and of biological efficiency; in the case of bromoxynil, this particle size corresponds to an average size of the particles of 1 to 10 μm, preferably of about 2 μm, preferably no particle being larger than 5 μm.

Starting from technical grade butraline, the procedure is analogous and the final size of the particles of butraline is preferably lower than about 5 μm.

The dry matter concentration of the mixture is selected in order to obtain the optimum performances of the mill; it may reach 75% by weight.

As soon as the desired particle size is obtained, the water-soluble film forming composition proper is prepared, that composition being intented to provide a brittle film. To achieve that result, binding agents, diluting agents as well as soluble fillers adapted to adjust the dose of active materials are introduced.

Lignosulphonates and polynaphthylmethanesulphonates are perfectly adapted as well as binding agents and as diluting or dispersing agents; thus, they are binding agents in the dry state and dispersing agents in the dissolved state; however, other soluble polymers may also be appropriate.

The soluble fillers may consist in mineral or organic sodium, potassium or ammonium salts, in other words in chlorides, sulphates or acetates but also in water-soluble organic products such as sugars or polysaccharides.

The above products recited in connection with the crushing are perfectly appropriate; however, their global dosis is in that case higher, from about 5 to 50% and preferably from 10 to 20% by weight with respect to the composition.

Finally, there is added, if necessary, small particles or fine size fillers, spreading products and biological adjuvants which do not necessitate crushing.

In the same way as previously, the use of products which could trouble the drying or alter the mechanical properties of the dried products is avoided.

Furthermore, the viscosity of the dispersion is adjusted by addition of water in order to obtain a fluidity authorizing a spreading in form of a thin layer; experience has shown that the most interesting results are obtained when using layers weighing several hundreds of grams/m$^2$, which corresponds advantageously to the thickness of a layer of paint.

Such a layer or coating can be obtained by any classical mean authorizing the spreading of a paint; it is possible to mention in that respect the application with a paint brush or with a paint roller or still again by mechanical or pneumatical spraying.

The surface characteristics of the support are also important; from a general point of view, the surface of the support must be anti-adherent.

In the general case, it is possible to use a support whose surface is not anti-adherent by itself; but, in that case, it is necessary to apply on the said surface a layer of a material which is anti-adherent, for instance based on silicone.

Such a surface can be regenerated when necessary by applying a new amount of anti-adherent product, for instance based on silicone.

The best results are obtained on supports comprising a teflon based anti-adherent coating; however, smooth or varnished surfaces are also appropriate.

In the lab, the drying can be carried out in an aerated stove.

Industrially, a drum or an endless belt can be used, the heating being carried out by way of radiating panels or hot air blowing.

In that respect, the installation shown on FIG. 1 has provided good results.

That installation comprises a drying drum 1 rotating around an axis XY in the direction of the arrow $F_1$; this drum which comprises a coating which is anti-adherent with respect to the applied products once dried, is located inside an enclosure 2 which is aerated by way of blowing devices 3, 4.

The dispersion D of particle of active substance is stored in a tank 5 located, in a first zone, inside the enclosed space or chamber 2; the application of the dispersion on the drying drum is carried out using a roller 6, rotating around an axis $X_1Y_1$ in the direction of the arrow $F_2$, the said roller dipping in the dispersion D.

In a second zone, the enclosure 2 comprises radiating panels 7 for the drying of the layer of dispersion of active material, these panels being arranged in such a way that they heat the drum avantageously on about one third of its perimeter.

The enclosed space 2 comprises, in a third zone, means to carry away the dried flakes P which detach from the surface of the drum due to the shrinking of the dried coating or layer; these means advantageously comprise a chute 8 wherein the transportation of the flakes P can be carried out by an endless screw 9.

Finally, the installation comprises cleaning devices for the drum 1, for instance a pad 10 which is applied by smooth friction against the surface of the drum and which is located downstream in the direction of rotation according to $F_1$ with respect to the chute 8.

The installation works as follows.

The drum 1 is rotated along $F_1$ by non shown acting means.

Using the coating roller 6, a coating consisting of the dispersion is continuously applied on the surface of the drum; during the rotation of the said drum in the direction $F_1$, the coating of dispersion applied on the surface of the drum travels through the zone which is heated by the panels 7. Under the influence of this heating, the dispersion coating cracks due to the shrinking and detaches from the surface, forming flakes P which are drained off through the chute 8.

The thus obtained material consisting of the flakes P has the aspect of fine flakes; under the effect of mild mechanical treatments, the biggest particles break without providing too fine particles.

The speeds dilution of the flakes when being put into contact with water is very favourable due to their big surface; said speed is not a function of the size of the flakes but only of their thickness; thus, for a given coating thickness, obtained by adjusting the employed amount, the product as obtained is not necessarily subjected to further crushing or calibrating, and no recycling of the flakes which are too big or too small is to be contemplated.

Figure 2:
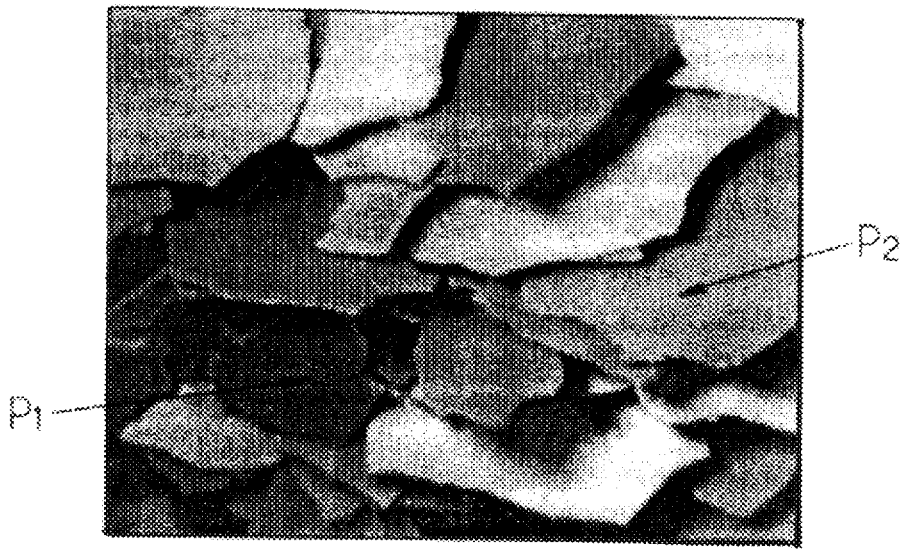
FIGS. 2 and 3 show the shape of the fine flakes according to the invention.
Figure 3:

The configuration or shape of the flakes according to the invention clearly appears from FIGS. 2 and 3 which are reproductions of photographs taken with an electronical microscope; they respectively show two sets of flakes of the solid storage and manufacturing presentation according to the invention.

Flakes $P_1$ which have a dark aspect and flakes $P_2$ which have a light or clear aspect can be distinguished; the dark aspect is that of the side by which the- flake adhered on the support at the moment of the manufacture; the clear aspect is that of the side by which the flake did not adhere to the support.

Furthermore, FIGS. 2 and 3 show the absence of dusty particles in the storage and manufacturing presentation according to the invention.

In the following examples:

bromoxynil, in other words 3,5-dibromo-hydroxybenzonitrile, is the one manufactured by C F P I and referenced CAS (Chemical Abstract Service) 1689-84-5, the butraline used is a technical butraline marketed by C F P I and whose its melting point is 59° C.; it is referenced CAS 33629-47-9, the products which are respectively denoted by the trademarks GALORYL MT 800 on the one hand, GALORYL DT 201 and GALORYL DT 505 on the other hand, are as the first is concerned wetting agents and as the seconds are concerned dispersing agents having binding- properties at the moment of drying; these products are manufactured and marketed by C F P I, the product denoted by the trademark MORWETT EFW is a wetting agent marketed by the Company Witco, the product denoted by the trademark TIXOSIL 38 is a precipitated silica marketed by Rhone-Poulenc, the sodium lignosulphonate which is a soluble product having a dispersing and binding effect, is the one which is marketed by Boregaard Company, the product denoted DIURON consists of the (dichloro-3,4-phenyl)-3-dimethyl-1,1-urea marketed by Rhône-Poulenc; DIURON is referenced CAS 330-54-1, the product denoted TITUS is a post-emergence herbicide for corn containing 25% of RIMSULFURON and marketed by Du Pont de Nemours.

EXAMPLE 1

An aqueous dispersion of brosoxynil of technical grade having the following composition is prepared:

technical grade bromoxynil containing 90% of active material and 7.5% of humidity . . . 1500 g
GALORYL MT 800 . . . 2.5 g
1GALORYL DT 505 . . . 75 g
tap water . . . 990 g This dispersion is prepared using a homogenizing device for laboratory of the trademark SILVERSON and by incorporating progressively the bromoxynil powder in the solution of the two surface-active agents. It is then refined on a ball-mill of brand DYNO-MILL until the moment at which the observation under microscope does no longer show the presence of particles having a size higher than 5 microns.

An amount of 800 g of said dispersion is taken and mixed with 100 g of sodium lignosulphonate.

The resulting aqueous dispersion is sprayed by means of an aerosol generator of the brand SIGMA SPRAY on aluminum panels whose dimensions are 28 cm×38 cm and which comprise on anti-adherent coating of the household type; these panels are previously heated to 50° C.

After deposit by progessive spraying of a homogeneous layer having a weight of 200 to 250 g per $m^2$ (that is to say 20 to 25 g per panel), drying is carried out inside an aerated oven at 75° C.

The coating shrinks and detaches witout effort forming small flakes, these flakes are subjected to a mild mechanical treatment, such as for example crushing by means of a rubber stop due to which their dimensions are reduced without emission of fine dust.

The storage and marketing presentation thus obtained dilutes easily in less than one minute when it is thrown into water and the examination under a microscope of the thus obtained slurry shows that the solid particles of active substance are perfectly redispersed.

EXAMPLE 2

An aqueous dispersion of bromoxynil of technical grade and of high concentration and having the following composition:

| | |
|---|---|
| technical grade bromoxynil containing 90% of active material and 7.5% of humidity | 1500 g |
| MORWETT EFW | 2.5 g |
| GALORYL DT 505 | 7.5 g |
| tap water | 500 g | is prepared by progressively mashing the active substance in the aqueous solution of the surface-active agents.

The thick mixture thus obtained is crushed in a drum mill device of trademark AUREC under stirring together with a crushing filler consisting of hard ceramic cylinders during 10 hours. At the end of that crushing, the observation under microscope shows that the average size of the particles is of about 2 microns.

Simultaneously, there is prepared a mixture containing:

| | |
|---|---|
| TITUS at 25% of RIMSULFURON | 3.9 g |
| GALORYL DT 201 | 9.1 g |
| TIXOSIL 38 | 1 g |
| tap water | 19 g |

The totality of that mixture (33 g) is mixed with 67 g of the abovesaid dispersion of bromoxynil.

The thus obtained aqueous dispersion is sprayed using an aerosol generator of the trademark SIGMA SPRAY on aluminum panels whose dimensions are 28 cm×38 cm and which comprise an anti-adherent coating of the household type; these panelsire previously heated to 50° C.

After deposit by progessive spraying of a homogeneous coating representing 200 to 250 g per m² (that is to say 20 to 25 g per panel), drying is carried out inside an aerated oven at 60° C.

The coating shrinks and detaches witout effort forming small flakes which are subjected to a mild mechanical treatment, such as crushing with a rubber stop permitting to reduce their dimensions without emission of fine dust.

The storage and marketing presentation thus obtained dilutes easily in less than one minute when it is thrown into water and the examination under a microscope of the thus obtained slurry shows that the solid particles of active substance are perfectly redispersed.

EXAMPLE 3

An aqueous dispersion of DIURON having the following composition:

| DIURON of technical grade at 98% of active material | 622.2 g |
| --- | --- |
| GALORYL DT 505 | 50 g |
| GALORYL MT 800 | 10 g |
| tap water | 317.8 g | is prepared.

The surface-active agents are dissolved in water and the DIURON powder is progressively added. The operation is carried out using a homogeneizer for laboratory of the trademark SILVERSON.

Then a crushing step is carried out during one hour using a vertical ball-mill of the trademark SUSSMEYER. The examination under the microscope of the thus obtained dispersion confirms that the average size of the particles of the active substance is equal to 2 microns.

One part of that suspension is used for the preparation of a sprayable formulation whose constitution is as follows:

| dispersion of crushed DIURON | 131.2 g |
| --- | --- |
| GALORYL DT 505 | 10.5 g |
| eau de ville | 30 g |

The thus obtained aqueous dispersion is sprayed using a aerosol generator of the trademark SIGMA SPRAY on aluminum panels whose dimensions are 28 cm×38 cm and which comprise an anti-adherent coating of the household type; these panels are previously heated to 50° C.

After deposit by progessive spraying of a homogeneous layer representing 200 to 250 g per m² (that is to say 20 to 25 g per panel), drying is carried out inside an aerated oven at 60° C.

The coating shrinks and detaches witout effort, forming small flakes which are subjected to a mild mechanical treatment, such as crushing using a rubber stop permitting thus to reduce their dimensions without emission of fine dust.

The storage and marketing presentation thus obtained dilutes easily in less than one minute when it is thrown into water and the examination under a microscope of the thus obtained slurry shows that the solid particles of active substance are perfectly redispersed.

Another part of the said suspension is used to prepare a formulation which is more concentrated and whose composition is as follows:

| dispersion of crushed DIURON | 84.2 g |
| --- | --- |
| GALORYL DT 505 | 15.2 g |

The thus obtained cream is applied, using a roller of alveolar foam, on an aluminum panel comprising a coating consisting of teflon, the said panel being then dried in an aerated stove at 50° C. during 6 hours.

After drying, the flakes as obtained are recovered using a flexible plastic blade; the flakes are then refractionated in order to bring their biggest dimension to less than 1 cm.

The dilutement of these flakes in water is total.

EXAMPLE 4

An aqueous dispersion of technical grade butraline having a melting point of 59° C. and the following composition:

| butraline at 98.5% of active material | 500 g |
| --- | --- |
| GALORYL DT 505 | 45 g |
| tap water | 455 g | is prepared.

First, GALORYL is dissolved in water and butraline previously crushed to a particle size of 0.5 mm is progressively added under stirring.

The thus obtained mixture is crushed using a vertical ball-mill of the trademark SUSSMEYER energically cooled so as to maintain at 25° C. the temperature of the mixture during the crushing. Examination under the microscope of the thus obtained suspension of active material shows that the particule size of the active material is lower than 5 microns.

One part of that suspension is used for the preparation of a sprayable formulation containing:

| suspension of crushed butraline | 888 g |
| --- | --- |
| GALORYL DT 505 | 96 g | by dissolution of the supplemental amount of GALORYL in the said suspension.

By spraying of this formulation on aluminum panels comprising an anti-adherent coating, an homogeneous layer is progressively formed; to spray the said formulation, an aerosol generator of the trademark SIGMA SPRAY is used, the evaporation of propulsive gas reducing the temperature of the sprayed product of about 5° C. below the ambient temperature.

Drying is carried out by air at 22° C. and 40% of relative humidity circulating above said panels at a speed of 2 m/sec.

The coating begins to shrink and to detach after a few minutes drying is continued during 30 minutes.

The storage and marketing presentation thus obtained under the form of flakes does not generate dust and, when it is thrown into water, dilutes completely in less than one minute providing a fine, stable and homogenous dispersion.

We claim:

1. Phytosanitary composition consisting of thin flakes whose thickness is from 50 to 400 μm and whose largest dimension is from 2 to 20 mm, said thin flakes which are based on a water-soluble film-forming material which provides after drying a shrinking brittle film comprising therein dispersed particles of at least one active substance which is little soluble or insoluble in water and solid at ambient temperature, the largest dimension of said particles being from 1 to 10 μm.

2. Phytosanitary composition according to claim 1, wherein the at least one active substance is an herbicide.

3. Phytosanitary composition according to claim 1, wherein the at least one active substance is selected from the group consisting of bromoxynil, ioxynil, bromoxynil esters, ioxynil esters, bromoxynil octanoate and ioxynil oxtanoate.

4. Phytosanitary composition according to claim 1, wherein the at least one active substance is selected from the group consisting of dinitroanilines, butralin, pendimethalin, flumetralin and oryzalin.

5. Phytosanitary composition according to one of claims 1 to 4, wherein the thickness of the flakes is from 100 to 200 μm.

6. Phytosanitary composition according to one of claims 1 to 4, wherein the largest dimension of the particles of active substance is from 2 to 5 μm.

7. Process for the preparation of a phytosadtary composition according to claim 1, wherein a dispersion of particles of the at least one active substance in an aqueous solution of a film-forming material which is water-oluble and brittle in the dry state and which comprises the other components of the phytosanitary composition, is spread over a surface anti-adherent with respect to the said dispersion once dried in such a way that it forms a layer whose thickness is from 50 to 500 μm, the said layer being then subjected to a drying at a temperature from 35° to 150° C., the said layer, once dry, shrinking and separating itself from the support forming thus thin flakes.

8. Process according to claim 7, wherein the thickness of the layer is from 100 to 300 μm.

9. Apparatus for the preparation of a phytosanitary compositions according to claim 1, comprising, inside of an enclosed space or chamber (2), a rotating drying drum (1) comprising a surface which is anti-adherent with respect to the product, once dry, intended to be spread thereon means (6) adapted to apply continuously, inside a first zone which is not heated, of the enclosed space (2), at the surface of the drum (1), a thin layer of a dispersion (D) of particles of at least one active substance in an aqueous solution of a film-forming material which shrinks on drying, which is brittle at the dry state and which also comprises the other components of the phytosanitary composition, heating means (7) for the surface of the drum located inside a second zone of the enclosed space or chamber and inside a third zone meant (8, 9) for recovery of the thin flakes formed after drying from the layer of aqueous dispersion spread on the surface of the drum (1) and means which are adapted to rotate the drum in such a way that the parts of the surface of the drum-on which is applied the abovesaid dispersion travel through the heated part or zone of the chamber at a speed such that the dispersion (D) is dried, shrinks and becomes detached from the surface of the drum, forming thus flakes (P).

* * * * *